(12) United States Patent
Bolmsjö et al.

(10) Patent No.: US 6,524,270 B1
(45) Date of Patent: Feb. 25, 2003

(54) METHOD AND DEVICE FOR THE TREATMENT OF PROSTATE TISSUE

(75) Inventors: Magnus Bolmsjö, Lund (SE); Sonny Schelin, Rockneby (SE)

(73) Assignee: Prostalund Operations AB (SE)

( * ) Notice: Subject to any disclaimer, the term of this patent is extended or adjusted under 35 U.S.C. 154(b) by 0 days.

(21) Appl. No.: 09/526,389

(22) Filed: Mar. 16, 2000

(30) Foreign Application Priority Data

Dec. 23, 1999 (SE) ............................................. 9904800-1

(51) Int. Cl.$^7$ ................................................ A61B 18/18
(52) U.S. Cl. ........................ 604/22; 607/113; 607/116; 606/41
(58) Field of Search ................... 604/22, 19; 607/116, 607/113; 606/27, 28, 32, 41

(56) References Cited

U.S. PATENT DOCUMENTS

| 5,249,585 A | * 10/1993 | Turner et al. ............ 607/113 X |
| 5,366,490 A | 11/1994 | Edwards et al. |
| 5,370,675 A | 12/1994 | Edwards et al. |
| 5,413,588 A | 5/1995 | Rudie et al. |
| 5,800,493 A | * 9/1998 | Stevens et al. ............. 607/113 |
| 5,964,791 A | 10/1999 | Bolmsjo |
| 6,119,045 A | * 9/2000 | Bolmsjo .................... 607/156 |

FOREIGN PATENT DOCUMENTS

| EP | 0462302 A1 | 12/1991 |
| SE | 505332 | 8/1997 |
| WO | WO 92/18199 | 10/1992 |
| WO | WO 99/07315 | 2/1999 |

* cited by examiner

*Primary Examiner*—Kevin Lee
(74) *Attorney, Agent, or Firm*—Mathews, Collins, Shepherd & McKay, P.A.

(57) ABSTRACT

A device for treatment of the prostate, comprising a catheter for treatment which is inserted through the urethra. The treatment catheter being provided with a front portion that comprises an expandable container for fixation of treatment catheter with a front portion in the urinary bladder and with a drainage channel ending in the front portion for drainage of urinary bladder. At least one hollow tip is provided to be extendible from treatment catheter into the surrounding prostate tissue of catheter. The tip is connected with a syringe for supply of an astringent and analgesic medicine. By this method, tip is extended from the treatment catheter into the surrounding prostate tissue of catheter. An astringent and analgesic medicine is supplied from the syringe and administered to the prostate tissue through the tip.

11 Claims, 3 Drawing Sheets

METHOD AND DEVICE FOR THE TREATMENT OF PROSTATE TISSUE

TECHNICAL FIELD OF THE INVENTION

The invention concerns a method and device for heat treatment of bodily tissue.

Heat treatment yields good treatment results with certain types of disease conditions involving unnatural growth of tissue. The tissue is heated to the extent that it dies. Examples of such disease conditions are certain types of cancer and benign prostate hyperplasy, BPH. During treatment certain portions of the tissue are heated so that tissue death ensues, while other portions of tissue must or should be protected. The temperature in the area of treatment should amount to at least 50° C. The duration of treatment is typically 1 hour but could be shorter. The disease conditions which are primarily indicated are those which occur in tissue surrounding cavities in the body, such as the prostate gland.

STATE OF THE ART

Different devices can be used in order to induce heating. Devices for heating by means of laser as well as with microwaves and radio frequencies are common.

Heat treatment with a treatment catheter that is equipped with a microwave antenna is also known with the mentioned course of disease. Characteristic for previously known microwave treatment is that the prostate tissue is heated with microwaves. The intention is to heat parts of the prostate gland so that the tissue coagulates, i.e. dies. Examples of such microwave treatment are known previously through U.S. Pat. No. 5,480,417 and U.S. Pat. No. 5,234,004. The element that emits the microwave radiation consists of a coaxial cable that is included in a catheter for treatment. Cooling fluid circulates through the catheter. The intention with the cooling is to protect the prostatic urethra, that is to say the part of the urethra that runs through the prostate gland, from being affected and damaged by the heat that is generated by the microwaves. Another reason for cooling the catheter is to transport away waste heat in the coaxial cable. Also, cooling of the catheter has been suggested to yield pain relief, the effect being uncertain.

It has long been viewed as important to protect the prostatic urethra during microwave treatment of benign prostate enlargement. This protection of the prostatic urethra hinders the treatment from being really effective, however, since parts of the obstructing tissue closest to the urethra are not heated sufficiently but remain unaffected because of the cooling. The clinical result of heat treatment of the kind envisioned here is dependent on the amount of tissue that coagulates. The degree of coagulation depends in turn on temperature in combination with the length of treatment. The temperature in turn depends on the input of energy and the heat dissipation by the blood flow. If the purpose of cooling the prostatic urethra is to protect the urethra from destruction, the transport of heat energy away from the area of treatment is increased, which is counterproductive and in the end diminishes the efficiency of the treatment.

A medical device is known from U.S. Pat. No. 5,366,490. The device comprises a catheter that can be inserted through urethra to the prostate. A control channel for an extendible needle runs through the catheter. The needle may be equipped in its tip portion with, or designed as, a needle antenna for microwaves. The tip portion can extend into the prostate tissue. According to an alternate embodiment the needle may instead be hollow and used for the supply of treatment fluid to destroy cells in the prostate tissue. Pain relief is achieved in accordance with U.S. Pat. No. 5,366,490 by supplying a gel or similar into the urethra and, in the case of severe pain, by administering an anesthetic to the patient.

Problems may arise with different forms of heat treatment of BPH due to a large blood flow in the prostate tissue. A large blood flow results namely in heat from the treatment catheter being directed away from the tissue that was meant to be heated. This may lead to a problem with increased time for treatment or that the efficiency of the treatment deteriorates. Another aggravating circumstance is the fact that blood flow varies greatly from one individual to the other.

By measuring the temperature in the prostate tissue during treatment and by using a stronger or more directed supply of heat in those cases when the temperature does not increase in a desirable way, it is possible to maintain an acceptable result of treatment. Stronger supply of heat raises the temperature in certain portions of the prostate tissue. Treatment given in particular in the case of such further increased temperature may lead to severe pain in patients. In order to lessen such pain to some extent, a pain-relieving agent is generally administered in various ways preoperatively. It is for instance common to insert a gel containing an analgesic substance into and through the penis and urethra to an area around the prostate. Thus, a good analgesic effect can be obtained in the urethra. During the subsequent treatment the prostate tissue will, however, also be heated, which can result in the patient experiencing pain despite the preventive pain relief procedure.

Prior to this type of treatment of the prostate it is preferable to drain the urinary bladder. This is usually implemented by inserting a urinary catheter of conventional type through the urethra, so that one end thereof reaches into the urinary bladder. Upon emptying of the urinary bladder the catheter is removed and a treatment catheter is instead inserted into urethra. It is a disadvantage for the patient that several catheters are used in conjunction with the treatment. The patient may experience several changes of catheters as unpleasant and to some extent painful.

THE INVENTION IN SUMMARY

It is an objective of the invention to overcome the abovementioned problems. It is thereby possible according to the invention to obtain improved efficiency for treatment at the same time as the pain sensations of the patients are lessened.

According to one embodiment of the invention a combined anesthetic and treatment catheter is used. The treatment part thereof comprises a heating device inside a catheter sheath. Anesthesia of the prostate tissue is implemented by the use of at least one needle extending from the catheter sheath. The needle may be combined with temperature sensors.

According to a second embodiment there are no heating means present. Also in this embodiment there is a needle extendible from the catheter. The needle supplies medicine with a combined anesthetic and astringent effect.

BRIEF DESCRIPTION OF THE DRAWINGS

The invention will now be described in more detail with the aid of exemplary embodiments and with reference to the accompanying drawings, on which

THE INVENTION

Figure 1:
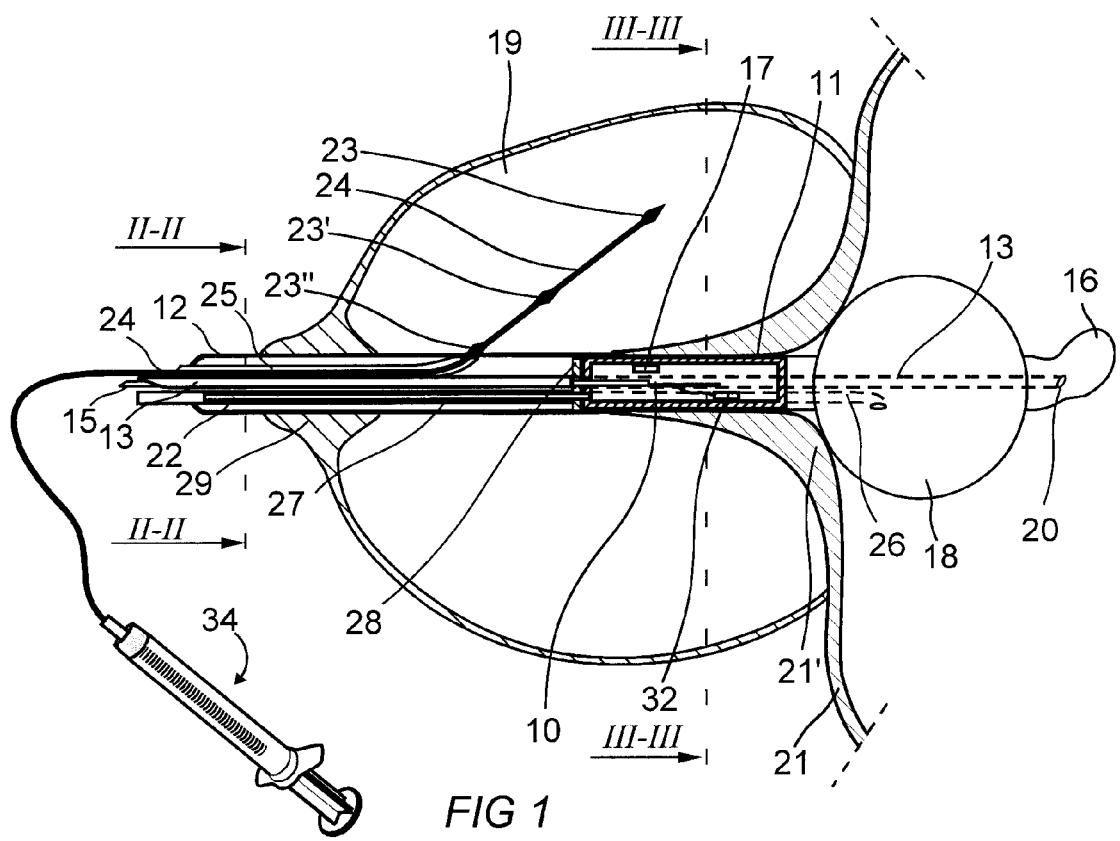
FIG. 1 is a side view partially in section of a first embodiment of a catheter according to the invention.

In the embodiment as per FIG. 1 a heating device 10 is provided inside a treatment catheter 12 for heating of tissue surrounding catheter 12. Heating device 10 can emit electromagnetic radiation preferably in the form of microwaves. Preferably heating device 10 comprises a microwave antenna. The heating device is enclosed in a chamber 11 filled with fluid. Fluid to chamber 11 can be supplied via a channel 22. Energy given off from heating device 10 is absorbed to a lesser extent by the fluid in chamber 11, but most of the energy irradiates and is absorbed in the surrounding tissue. Energy is supplied in a conventional way via a feed cable from an energy supply unit. In a preferred embodiment, the first heating device comprises an antenna that can be designed as, for instance, a unipolar, bipolar, or helical antenna. The antenna is covered all the way up to its irradiation portion by a casing to shield and decrease irradiation into other parts.

The active part of the treatment catheter is thus centrally located in the tissue that is to be treated, in this case in prostate 19 distal to the bladder neck 21'. The treatment catheter 12 is flexible and pliable in order to be introduced flexibly through the urethra to the treatment position. In the tip 16, or near it, there is an opening 20 made in catheter 12. A drainage channel 13 debouches into a first end in opening 20. A second end debouches outside of catheter 12. Urine is drained from the urinary bladder from drainage channel 13. In the first place, drainage of urine occurs prior to heat treatment. In the embodiment of the treatment catheter comprising heating device 10, drainage also occurs in the course of the treatment of the prostate tissue and also directly thereafter.

A first temperature sensor 23 is arrayed on carrier 24 in order to be able to track the temperature development during heat treatment. Carrier 24 can be extended through a channel or tube 25, which runs through the treatment catheter. Carrier 24 is preferably designed as a tip. It is also possible that said first temperature sensor 23 is embodied with, or as, a tip that can penetrate either a membrane or a wall in the treatment catheter and the bodily tissue. A second temperature sensor 23' is also provided on carrier 24 at a certain distance from the tip. Tube 25 is embodied so that carrier 24 with said first temperature sensor 23 and said second temperature sensor 23' is extended out of the treatment catheter at a suitable angle and can be driven out to a suitable distance from the treatment catheter. It is also possible to provide a special angled member at the end portion of tube 25 to attain the desired orientation of carrier 24 with temperature sensors 23 and 23'.

A third temperature sensor 23" is provided in connection with a wall of treatment catheter 12. In the illustrated embodiment said third temperature sensor 23" is provided on the carrier 24. A fourth temperature sensor 32 can be provided inside container 11 and preferably in a heat-conductive contact with container 11.

In the embodiment shown in FIG. 1 carrier 24 is hollow like a tube. In an interior space within tubular walls of the carrier, tubes 14 (see FIG. 2) for the temperature sensors are arranged. The interior space of carrier 24 is adapted for administration of a combined analgesic and astringent medicine to the prostate tissue. The medicine is supplied before heat treatment is started. As the carrier 24 is designed to be inserted with its first end far into the tissue to be treated, the medicine will have a very good effect both with regard to the desired analgesic effect and the desired astringent effect.

A second end of carrier 24 is connected in a location outside of the catheter to means for supply of medicines. Such a device can be a conventional syringe 34 to be connected to carrier 24 in conjunction with the treatment.

Figure 4:
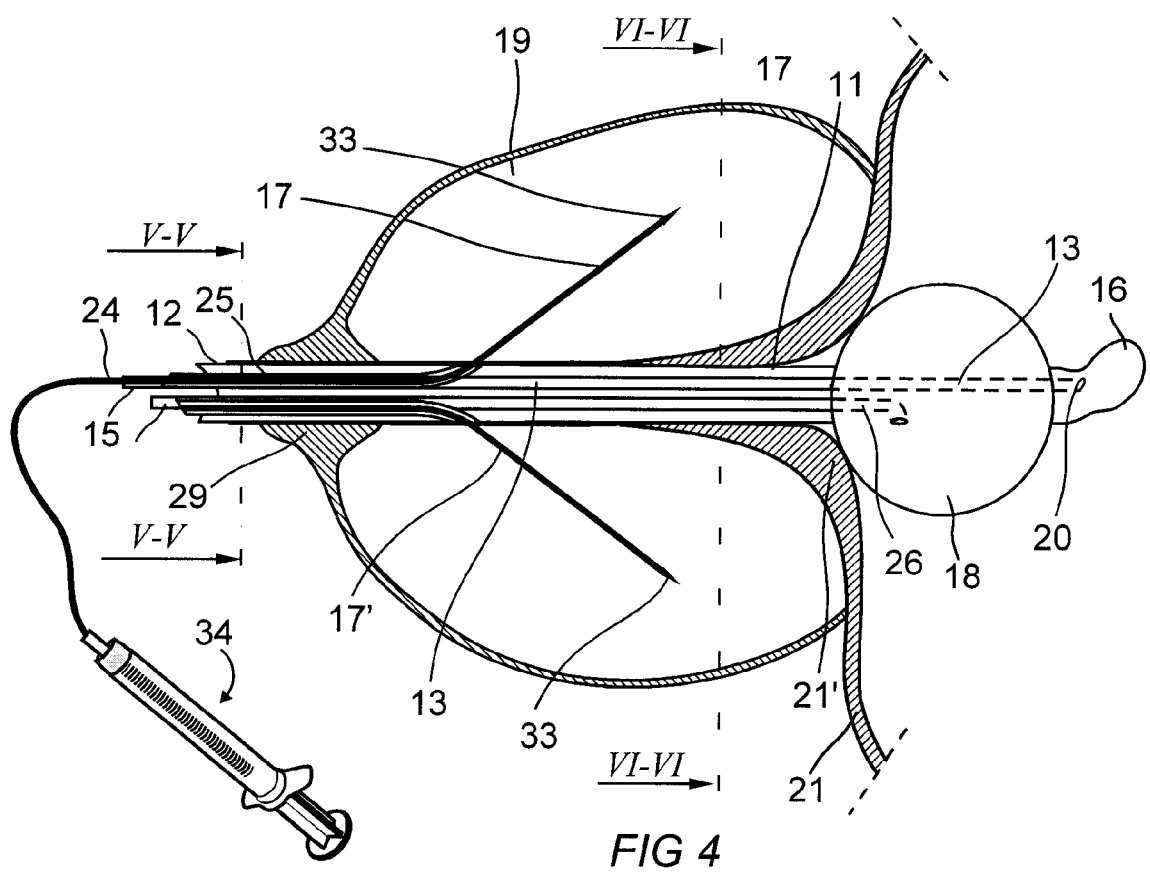
FIG. 4 is a side view partially in section of a second embodiment of a catheter according to the invention.

Since the prostate consists of two lobes, both should be treated with the anesthetic and astringent agent. According to the embodiment shown in FIG. 1 this is possible by pulling back carrier 24 to a position within the catheter casing after treatment of a first lobe. After that, the entire catheter is rotated 180° around its longitudinal axis and the carrier is extended into the second lobe. The treatment is concluded with the second lobe. It is within the scope of the invention also possible to provide two diametrically opposite tubes for carriers and in so doing enable simultaneous treatment of the two lobes. An example of such an embodiment is shown in FIG. 4.

In the treatment catheter, a fluid channel 26 that ends in balloon 18 is also present. See FIGS. 2 and 3. Fluid can be supplied through it for expansion of balloon 18 when the treatment catheter is brought into the desired position for treatment. Fluid channel 26 is also used in order to empty balloon 18 after treatment is completed and before the treatment catheter is withdrawn from the urethra. A conventional hypodermic needle or similar is suitably used for the filling and emptying of balloon 18.

Feed cable 15, through which first heating device 10 is supplied with energy, becomes hot as a result of cable losses. In order to avoid thermally induced injury to tissue because of these cable losses outside the area of treatment, for example on the sphincter muscle that surrounds the urethra outside the prostate or on the penis, feed cable 15 is cooled. This is accomplished by cooling channels 27 that are included in treatment catheter 12 (see also FIGS. 2 and 3), preferably around feed cable 15. Cooling channels 27 may have a delimitation wall 28, at which cooling fluid circulating in cooling channels 27 returns. In this way cooling of heating device 10 and reservoir 11 is prevented which, in turn, means that the power that has to be supplied from an energy supply unit can be decreased. With lower power levels the risk of malpractice is lessened along with injury to healthy tissue. Through the cooling channels also extend drainage channel 13, channel 22 for supply of fluid to chamber 11, tube 25 for carrier 24 and fluid channel 26 which is used to fill balloon 18.

Figure 2:
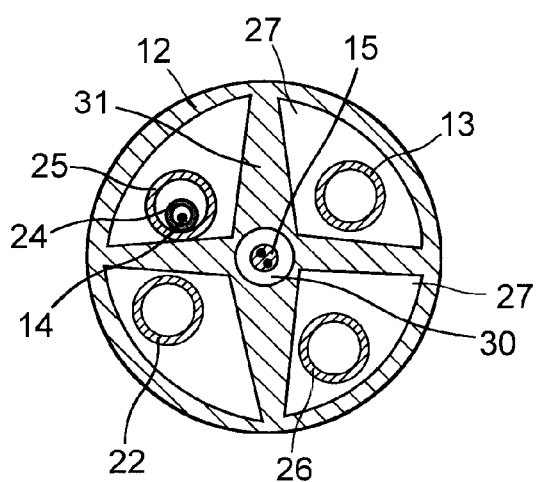
FIG. 2 is a sectional view from line II–II i FIG. 1.

FIG. 2 schematically shows a section of treatment catheter 12 of FIG. 1 from line II—II. Catheter 12 for treatment is provided with multiple cavities and channels extending lengthwise through the catheter. Feed cable 15, which preferably is well shielded, runs in a central cavity 30. A cooling liquid is transported preferably in a circulating system in four cooling channels 27 separated by partition walls 31. Tube 25 for carrier 24 is provided in a first cooling channel 27. In a similar fashion, fluid channel 26 for balloon 18, a channel 22 for chamber 11, and drainage channel 13 are arranged in other cooling channels 27. Several tubes and channels may also be provided in one and the same cooling channel.

Figure 3:
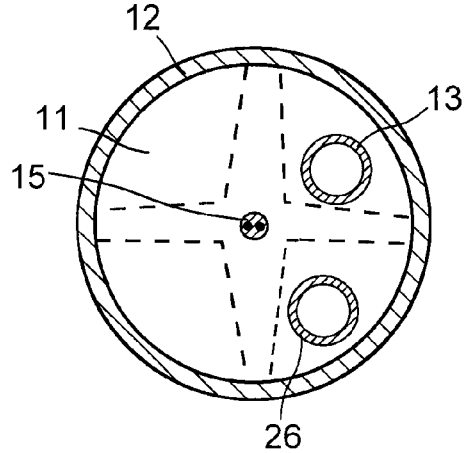
FIG. 3 is a sectional view from line III–III i FIG. 1.

The cross-sectional view of FIG. 3 illustrates an example of how chamber 11 can be designed. Virtually all of the interior of treatment catheter 12 is occupied by chamber 11. Intermediate partitions are indicated and may be used for example to guide feed cable 15, fluid channel 26 for balloon 18 and drainage channel 13. Alternatively, chamber 11 may consist of channel units bound together and constituting the continuation of cooling channels 27 beyond delimitation wall 28.

Feed cable 15 can be formed as a coaxial cable with a shielding covering and an inner conductor. The covering of the cable is also an outer conductor. The inner conductor continues beyond the end of the covering in the form of an antenna.

In the alternative embodiment of the invention according to FIG. 4 the catheter does not have a heating device. As for other features, the catheter comprises, in accordance with this embodiment, several components that are in accordance with the embodiment shown in FIGS. 1–3, and these, additionally, have the same designations of reference.

A difference with respect to the embodiment of FIGS. 1–3 is that a needle 17 is provided in lieu of carrier 24 and that this is enhanced with a second needle 17'. Needles 17, 17' represent tips in this embodiment. This enhancement enables both lobes of the prostate to be treated simultaneously with an analgesic and astringent medicine. Needle 17 is provided with a tip 33 which facilitates the penetration of bodily tissue. The needle, in the same fashion as in the above-described embodiment, is connected to a device, for example a syringe 34, external to the catheter for supply of a medicine.

Figure 5:
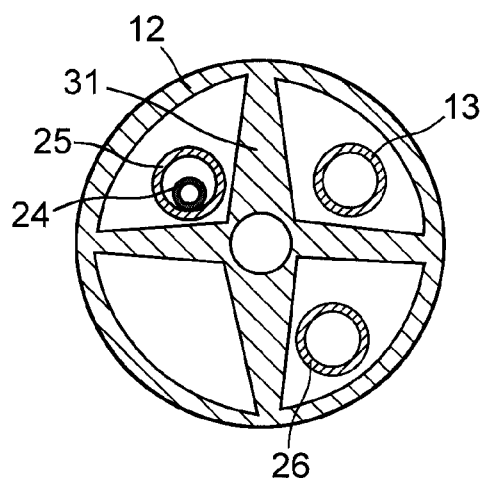
FIG. 5 is a sectional view from line V–V i FIG. 4.

The catheter according to FIG. 5 comprises, as does the above described catheter, partition walls 31. These facilitate handling of those carriers and/or needles, tubes, etc. which run through the catheter. The partitions may be omitted if no cooling is to be used.

A tube 25 extends in one of the spaces extending through the entire catheter between the partition walls 31. In this embodiment needle 17 runs in tube 25, which debouches in the catheter wall. Drainage channel 13 is occupied by an equivalent second space, and fluid channel 26 for balloon 18 extends in a third space. Balloon 18 is important also in this embodiment for correct localization of the catheter, so that needle 17 and needle 17', if so provided, are correctly positioned. By correctly positioning the needle the supply of the anesthetic and astringent medicine can also be ensured.

Figure 6:
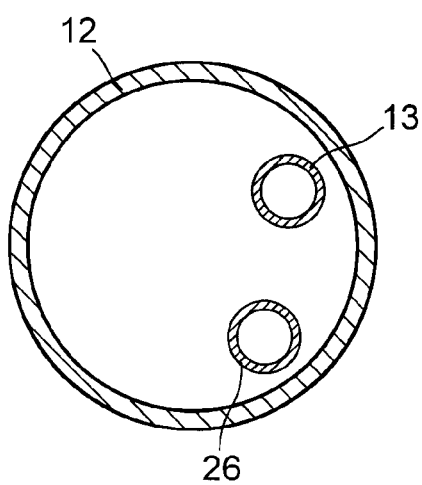
FIG. 6 is a sectional view from line VI–VI i FIG. 4.

It is indicated in FIG. 6 how catheter 12 can be designed in a portion of its axial extension or in its entire axial extension. There are no partition walls in this portion.

Figure 7:
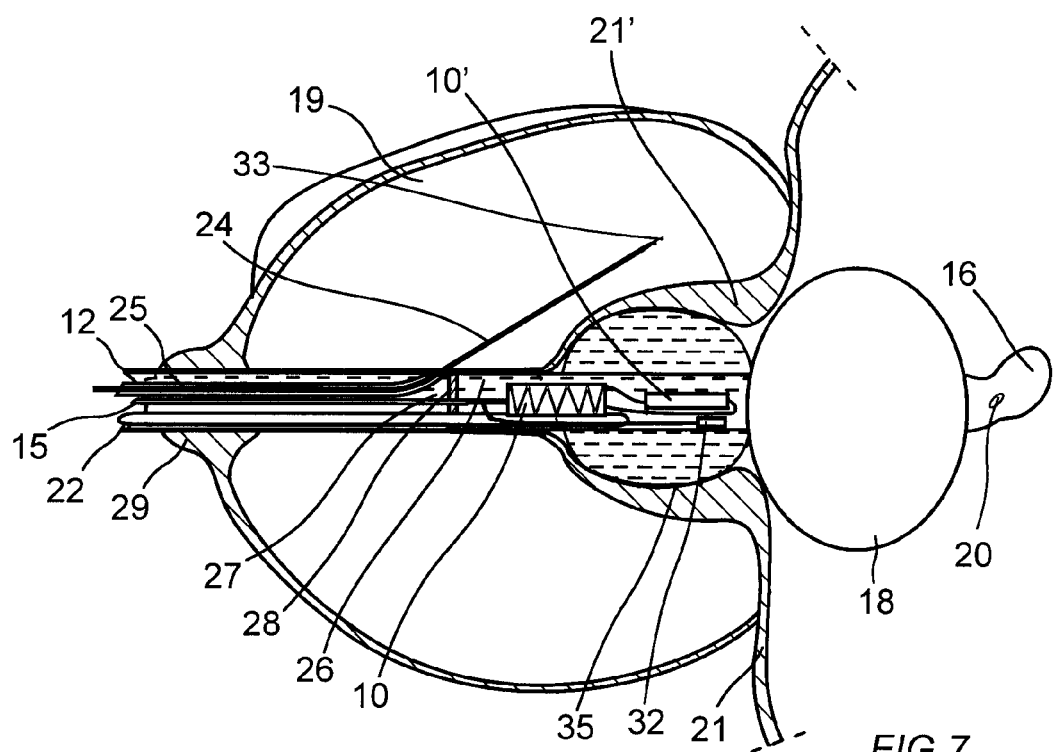
FIG. 7 is a side view partially in section of a third embodiment of a catheter according to the invention.

According to the embodiment shown in FIG. 7 treatment catheter 12 comprises a combined heating device in the form of a microwave antenna 10 and an electric heating element 10'. Microwave antenna 10 emits microwave radiation in a portion surrounding prostate tissue 19 for direct heating and destruction of this tissue. The electric heating element 10' emits heat to a fluid in a fluid container 35 which is provided external to and on the catheter. External fluid container 35 is powerfully distended and compresses the prostate tissue and bladder neck 21'. The flow of blood in the tissue is thereby decreased resulting in a higher efficiency of treatment. Furthermore, the engagement to the tissue is very good which increases the heat transfer to the tissue.

Upon insertion of medicine through carrier 24, this can be pulled back through tube 25. A carrier with a temperature sensor may instead be inserted through tube 25 according to the embodiment shown in FIG. 1, and extended out into the prostate tissue. Data from the temperature sensors are then used as described above. Microwave antenna 10 can be eliminated in embodiments wherein the electric heating element 10' and external fluid container 35 give off heat to an appropriate extent. Otherwise, the embodiment of FIG. 7 corresponds to embodiments described above, and the same reference designations have been used.

Figure 8:
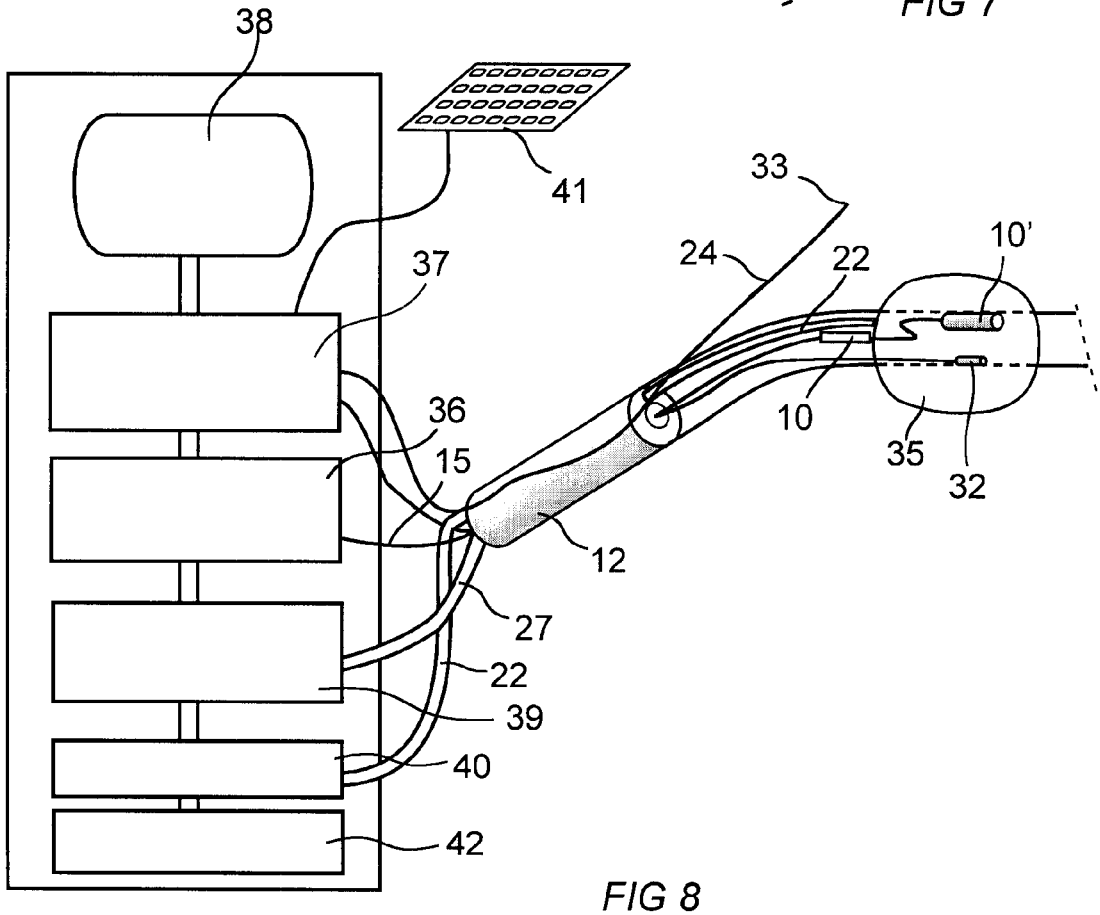
FIG. 8 is a principal block diagram of a control and drive unit for the treatment catheter.

The block diagram of FIG. 8 shows schematically the various function blocks that can be part of a treatment assembly having a catheter for treatment according to the invention. As stated above, energy is supplied to heating device 10, 10' from an energy supply unit 36. A central control unit 37 is operatively connected to the energy supply unit 36 and to a display unit 38 as well as to a pump and cooling device 39 and a water supply device 40. Control unit 37 is also operatively connected to an input device, for example a keyboard 41. Control unit 37, keyboard 41 and display unit 38 may also be included in a conventional computer equipped with a monitor and a keyboard.

Control unit 37 is operatively connected to temperature sensors 23 and 32 and, depending on the temperature of the area of treatment, can control the energy supply unit 36 in such a way that appropriate power is imparted to heating device 10. It will therefore be possible to increase the temperature in the external fluid container 35 with a good safety margin and, thus, in the surrounding tissue, so that death of the tissue will occur in the desirable way. Data regarding the temperature from temperature sensors 23 and 32 can also be presented continuously on display unit 38.

Pump and cooling device 39 are connected to cooling channels 27 and pump appropriate cooling liquid through cooling channels 27 to cool down primarily feed cable 15 in its extension to heating device 10. Fluid supply device 40 is used when external fluid container 35 is to be filled and distended. The filling can be monitored by control unit 37.

A preferred embodiment according to the invention also comprises a pressure gauge 42, which is operatively connected to fluid supply device 40. Pressure gauge 42 is also connected operatively to central control unit 37 so that the treatment process can be affected by the pressure in external fluid container 35. In addition, the pressure can be altered depending on how the treatment is proceeding. For safety reason it should be possible to interrupt the treatment if the pressure in fluid container 35 drops rapidly, for instance due to breakage.

Within the scope of the invention, embodiments according to FIGS. 1–3 may be combined in various ways with embodiments according to FIGS. 4–8. For example, it would be possible to provide double carriers with temperature sensors and an opening for the medicine to be applied. In embodiments comprising heating devices it is preferable to arrange at least one carrier with a temperature sensor so that the temperature development in the prostate can be monitored during the treatment. With data regarding the temperature development it is also possible to control the supply of heat from the heating device.

Temperature sensors 23, 23', 23", and 32 can in some or all of the examples of embodiments be designed as optical gauges or transducers. Carrier 24 may in such an instance comprise an optical fiber.

As soon as urine again passes through the urethra in the prostate the treated and dead tissue will be entrained and exit by the urine. A cavity remaining in the prostate from the removed tissue ensures proper passage of urine. The healing process including rejection of coagulated tissue may continue for a month or two.

What is claimed is:

1. A device for treatment of the prostate, comprising a treatment catheter which is inserted through the urethra, said treatment catheter being provided with a front portion that comprises an expandable container for positioning of said treatment catheter with said front portion in a urinary bladder, wherein at least one hollow tip is provided to be extendible from said treatment catheter into the prostate tissue surrounding said treatment catheter, and said tip is connected with a syringe for supply of an astringent and analgesic medicine.

2. The device according to claim 1, wherein two hollow tips are provided to be extendible in two diametrically opposite directions from said treatment catheter.

3. The device according to claim 1, wherein a hollow tip is provided to be repeatedly extendible from said treatment catheter into the prostate tissue surrounding said treatment catheter and again retractable into said treatment catheter.

4. The device according to claim 1, wherein first heating means is provided internally to said treatment catheter at such a distance from the container that heating of at least a central portion of the prostate tissue located around said treatment catheter is achieved by supplying energy to said heating means, said tip comprising a carrier supporting several temperature sensors.

5. The device according to claim 4, wherein said carrier supports a tube for the temperature sensors.

6. The device according to claim 1, wherein a fluid container expandable with a fluid is provided externally to and on said treatment catheter, and electric heating means is provided internally to said treatment catheter at such a distance from external container that heating of at least a central portion of the prostate tissue located around said treatment catheter is achieved by supplying energy to electric heating means.

7. A method for treatment of the prostate, comprising the following steps:

a) insertion of a treatment catheter through the urethra, said treatment catheter being provided with a front portion which comprises an expandable container, b) positioning said treatment catheter with said front portion in the urinary bladder and with a drainage channel debouching in the front portion for drainage of the urinary bladder, the method comprising the following steps:

i) extending at least one hollow tip from the treatment catheter into the surrounding prostate tissue of the treatment catheter, and ii) supplying an astringent and analgesic medicine from a syringe and administration of the medicine to the prostate tissue through said tip.

8. The method for treatment of the prostate as claimed in claim 7, further comprising the steps:

i) retracting said tip to a position inside said treatment catheter, ii) rotating said treatment catheter 180°, iii) extending the hollow tip from said treatment catheter into the surrounding prostate tissue of said treatment catheter, and iv) supplying an astringent and analgesic medicine from said syringe and administration of the medicine to the prostate tissue through said tip.

9. The method for treatment of the prostate as claimed in claim 7, further comprising the following steps:

i) extending two hollow tips in opposite directions from said treatment catheter into two lobes of the surrounding prostate tissue of said treatment catheter, and ii) supplying an astringent and analgesic medicine from said syringe and administration of the medicine to the prostate tissue through said tip.

10. A method for treatment of the prostate, comprising the following steps:

a) insertion of a treatment catheter through the urethra, said treatment catheter being provided with a front portion which comprises an expandable container, b) positioning of said treatment catheter with said front portion in the urinary bladder, the method comprising the following steps:

i) extending of at least one hollow tip from the treatment catheter into the surrounding prostate tissue of the treatment catheter, said tip is connected with a syringe, and ii) supplying an astringent and analgesic medicine from said syringe and administration of the medicine to the prostate tissue through said tip.

11. A method for treatment of the prostate as claimed in claim 10, further comprising the following steps:

i) retracting said tip to a position inside said treatment catheter, ii) rotating said treatment catheter 180° around a longitudinal axis, iii) extending the hollow tip from said treatment catheter into the prostate tissue surrounding said treatment catheter, and iv) supplying an astringent and analgesic medicine from said syringe and administering the medicine to the prostate tissue through said tip.

* * * * *